(12) United States Patent
Pang et al.

(10) Patent No.: US 11,791,048 B2
(45) Date of Patent: Oct. 17, 2023

(54) MACHINE-LEARNING-BASED HEALTHCARE SYSTEM

(71) Applicant: Anima Group Inc., Wilmington, DE (US)

(72) Inventors: Shun Pang, London (GB); Rachel Mumford, London (GB)

(73) Assignee: Anima Group Inc., Wilmington, DE (US)

( * ) Notice: Subject to any disclaimer, the term of this patent is extended or adjusted under 35 U.S.C. 154(b) by 0 days.

(21) Appl. No.: 17/693,097

(22) Filed: Mar. 11, 2022

(65) Prior Publication Data

US 2022/0293272 A1  Sep. 15, 2022

Related U.S. Application Data

(60) Provisional application No. 63/161,213, filed on Mar. 15, 2021.

(51) Int. Cl.
| | |
|---|---|
| *G16H 50/20* | (2018.01) |
| *G16H 10/20* | (2018.01) |
| *G16H 40/20* | (2018.01) |
| *G16H 15/00* | (2018.01) |
| *G16H 50/30* | (2018.01) |

(52) U.S. Cl.
CPC ............. *G16H 50/20* (2018.01); *G16H 10/20* (2018.01); *G16H 15/00* (2018.01); *G16H 40/20* (2018.01); *G16H 50/30* (2018.01)

(58) Field of Classification Search
CPC ........ G16H 50/20; G16H 50/30; G16H 10/20; G16H 15/00; G16H 40/20

USPC .......................................................... 705/2
See application file for complete search history.

(56) References Cited

U.S. PATENT DOCUMENTS

| | | | |
|---|---|---|---|
| 11,195,616 B1 * | 12/2021 | Seemakurty | ........... A61B 5/318 |
| 2018/0119137 A1 * | 5/2018 | Matsuguchi | ......... C12Q 1/6874 |
| 2018/0189457 A1 * | 7/2018 | Plummer | ............... G16H 50/20 |
| 2019/0034591 A1 | 1/2019 | Mossin et al. | |
| 2019/0392951 A1 * | 12/2019 | Jain | ...................... C12Q 1/6883 |
| 2021/0344880 A1 * | 11/2021 | Katra | ..................... A61B 90/98 |

(Continued)

FOREIGN PATENT DOCUMENTS

WO  WO-2020168018 A1 *  8/2020

OTHER PUBLICATIONS

Możejko et al. "Inhibited softmax for uncertainty estimation in neural networks." arXiv preprint arXiv:1810.01861 (2018) (Year: 2018).*

(Continued)

*Primary Examiner* — Jonathon A. Szumny
*Assistant Examiner* — Christopher B Wehrly
(74) *Attorney, Agent, or Firm* — MORRISON & FOERSTER LLP

(57) ABSTRACT

A method for providing a healthcare system. The method comprises a machine learning system: obtaining and labelling patient data to produce labelled patient data relating to one or more patients; determining one or more predictions based on the labelled patient data; receiving, from a user, one or more user inputs labelling each of the one or more predictions as a success or a failure; generating training data based on the labelled patient data and the one or more user inputs; and training the machine learning system based on the training data.

16 Claims, 10 Drawing Sheets

(56) References Cited

U.S. PATENT DOCUMENTS

2022/0093255 A1\* 3/2022 Molony ................. G16H 50/70
2022/0139530 A1\* 5/2022 Kollada ................. A61B 5/055
　　　　　　　　　　　　　　　　　　　　　　　705/2

OTHER PUBLICATIONS

ChristopheGS, "Deploying Machine Learning Models in Shadow Mode" (2020) (Year: 2020).\*

\* cited by examiner

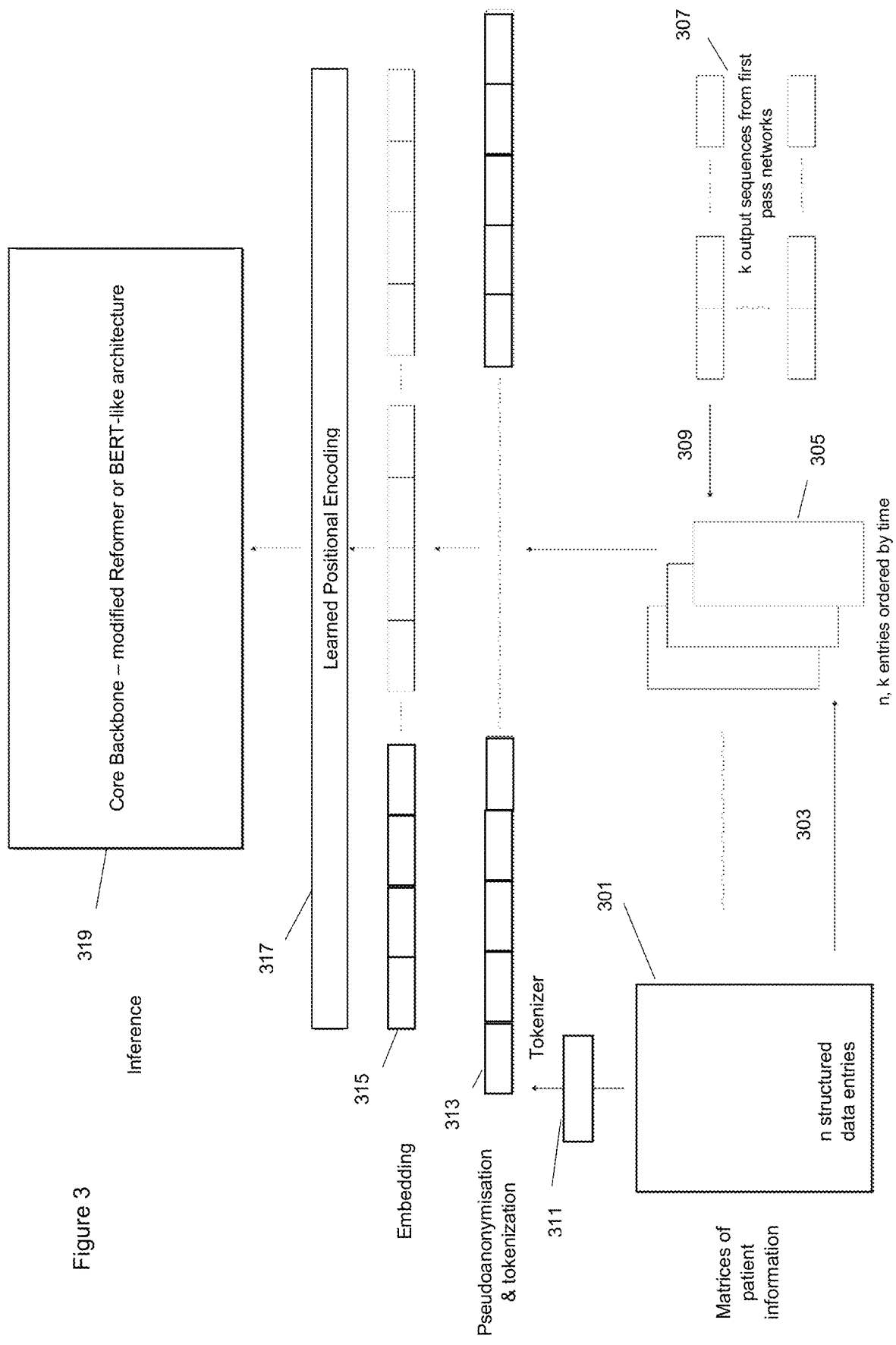

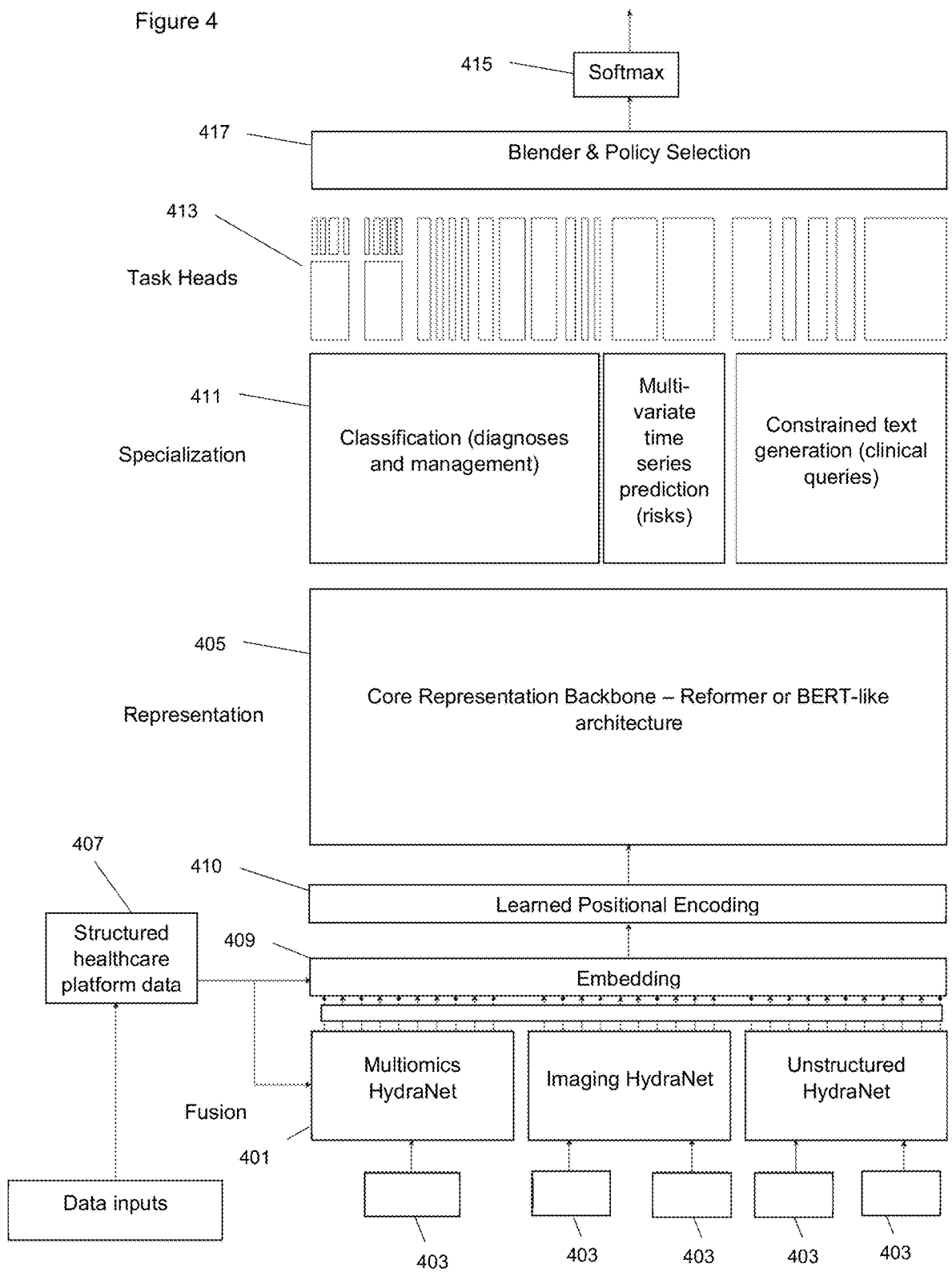

Herne Hill Medical Practice

Chloe Heath   DOB: 1993-08-03

[REPORT BUG] [LOG OUT] [Notifications (4)]

☐ Dashboard

◇ FAQ

I want to...

| Get help for a medical issue | Get a repeat prescription or admin request | Help myself thought online advice |

For example a new symptom or problem that's bothering you or to update your GP about an existing problem For example a sick note, doctor's note, getting a repeat prescription filed, test results, referrals Self-help advice and guides for any condition on the NHS website In Progress...

- Complete full asthma review — Click to complete review
- Action required: agree plan for Asthma Review.(2021-02-11) — Acknowledge
- Action required: agree plan for Asthma Review.(2021-02-11) — Acknowledge
- Action required: agree plan for Asthma Review.(2021-02-11) — Acknowledge
- Action required: agree plan for Asthma Review.(2021-02-11) — Acknowledge α anima

FIG. 5

Chloe Heath   DOB: 1993-08-03

Complete full asthma review for doctor at Herne Hill Medical Practice:

Okay. During the last 4 weeks, how often has asthma kept you from getting as much done at work, school or home?

| All the time | Most of the time | Some of the time | A little of the time | None of the time |

Under construction

Shun Pang | Born: Jun 8, 1993 | Sex: Male
NHS No.:- | GP:-

Review | Request more info

Routine review in primary care

Shun has asthma, and overall is doing well. They scored 25 out of 25 on the ACT, meaning their asthma is likely well controlled. Nil SOB past 2w. No rescue inhaler use past 4w. Nil A&E attendance for asthma in past 2y. Not a smoker. Current PEFR is unknown. Pt doesn't have a peak flow meter. Best PEFR is unknown. Overall, Pt reports excellent adherence. Uses preventer 7/7 days in typical week. Always uses preventer medication, even if feeling well. Pt feels very confident with inhaler technique (note - this self-reported confidence). Self-care action plan > 1 year old.

Recommendations: maintain current plan & resolve case.

Asthma - List
ACT: (Score: 25) Well controlled
Symptoms Index: (Score: 5) No SOB
Insight Index: (Score: 0.00) Good: perceived level of asthma matches actual ACT
Preventer Use: (Score: 7) Good: uses preventer every day
Adherence: (Score: 3) Good: always uses preventer, even when feeling well
Rescue: (Score: 5) No rescue use in the past 2 weeks Manage | Close

FIG. 8

MACHINE-LEARNING-BASED HEALTHCARE SYSTEM

CROSS-REFERENCE TO RELATED APPLICATION

This application claims the benefit of U.S. Provisional Application 63/161,213, filed on Mar. 15, 2021, the entire contents of which are incorporated herein by reference for all purposes.

FIELD OF INVENTION

Embodiments of the present disclosure relate to a healthcare system and a method for providing a machine-learning-based healthcare system.

BACKGROUND

Healthcare is on an unsustainable trajectory from a combination of demographic change, increased patient expectations and increased per capita chronic disease burden. Globally, health spending is outstripping GDP growth. Patients are having to pay more than they did ten years ago, and are finding it more difficult to access quality healthcare. For example, in the US, health insurance premiums have risen 71% in the past decade. Aside from cost, the supply/demand gap is growing larger. In the US for example, the clinical capacity shortfall is projected to worsen 600% by 2030. In short, there is a finite output of global clinical productivity/per unit time that can be utilized and this is currently insufficient to provide optimal care for all patients. It is also likely that this insufficiency will worsen in future.

Clinical decisions such as diagnosis, treatment or otherwise management of disease is determined through the available information that a clinician knows and understands, whether this be patient reported information, clinical examination, tests, or imaging, for example. The speed and quality of clinical decision making is therefore at least determined in part by the quality of this clinical information and how quickly the clinician can access and process it. Healthcare currently suffers from an information bottleneck, with the notable exception of acute inpatient settings where, conversely, too much information is the problem.

BRIEF SUMMARY

In order to provide an effective healthcare system that is applicable in the majority of circumstances, data flow between patients and healthcare professionals must be improved, and that healthcare productivity must improve in light of rising demand from demographic change, increasing patient expectations and increasing chronic disease burden.

Exemplary embodiment of the present disclosure include a healthcare system and machine learning system that serve as a means to improve data flow between patients and healthcare professionals and increase healthcare productivity, by autonomously reviewing patients with both new and ongoing chronic problems and producing actionable reports with recommendations & predicted risk profiles, much like how a human resident doctor would present their findings to the attending physician. This makes it possible for healthcare professionals to manage at least a portion of their patients in a fully asynchronous manner and much more rapidly than through a synchronous workflow where the physician must first take a detailed history—the outlined embodiments are able to take this history for them, and transform it into a digestible report. The authors hope that with sufficient and proven F1 score performance beyond that of human clinicians, the healthcare system could operate autonomously, diagnosing, managing and following up patients with minimal to no human intervention required.

The architecture for the healthcare system/machine learning system, including training and inference, is a significant element of the disclosure. The performance of the machine learning system is directly related to the quality and quantity of the training data used to train the model. It is widely held that 80% of the effort in an analytic model is preprocessing: merging, customizing, and cleaning datasets, not analyzing them for insights. Some embodiments of the present disclosure are therefore focused on methods for acquiring training sets of sufficient scale and quality required to train the machine learning system, and outlining how these methods improve over the state of the art. The claimed methods particularly address how the system improves on three key rate limiting steps of the existing state of the art: (1) acquiring and preprocessing high quality training examples that are feature complete, rapidly and inexpensively (2) acquiring the sufficient scale of training examples needed for a general healthcare AI, rapidly and inexpensively (3) ensuring that training sets are balanced towards weakly performing edge domains; creating a mechanism for recursive improvement of the model that is repeatable and scalable.

The methods for the healthcare system/machine learning system can be broadly divided into 4 stages: inference & failure detection, seeding, boosting and training. The described approach outlines methods in which all 4 stages, and therefore the entire training and inference architecture, may be fully automated.

Instead of acquiring training data from electronic health records through data mining, the healthcare platform acquires training data directly from patients, first hand, by being their point of access for care. Patients submit their problems through a web/mobile app and are taken through a gold standard history specific to their presentation. Instead of recording the history as free text, the platform collects highly structured categorical or ordinal answers that may directly be encoded unambiguously into tokens representing features. Unlike clinical notes, which vary wildly in quality, colloquialisms and completeness, data collected by the healthcare platform is always consistent, pre-structured and feature complete. This data is sent in the form of an abstracted clinical report for healthcare professionals to review and sign-off.

The described approach collects structured data on the clinical actions taken in response to each patient request, concatenates these to the patient's records and uses them as ground truth output targets for training the machine learning system through supervised imitation learning (another embodiment uses the actual clinical outcomes of patients as output targets). This negates any need to pay expensive doctors separately to data label patient records, which the authors have established is exceedingly cost prohibitive for anything but the narrowest of applications in highly specialized subdomains of medicine.

Mismatch between human clinical actions and the actions/predictions recommended by the machine learning system are used to calculate a cross-entropy loss for training the model, and also for identifying failure/edge cases. These failure cases are aggregated, clustered into discrete classes, and used as seed training sets for binary classifiers trained to identify further examples from the user network. These classifiers identify further examples, thus boosting the seed set into much larger training sets for the main model. This creates a negative feedback effect whereby likely failures are preferentially included in training sets of successive training epochs, ensuring that the system tends towards overall improvement; in other words, the training set is always reasonably well balanced.

After retraining the model, if it passes unit tests, the model is deployed in shadow mode and evaluated against human performance and that of the live machine learning system. If no regression has taken place, the new shadow branch may receive sign-off from a quality assurance team, and become live and available for inference on the user network. This completes the workflow and training loop.

A key advantage of the described approach is that there is minimal or no manual data pre-processing steps required, and edge cases/failures are automatically identified and automatically boosted into well-balanced training sets. This is in contrast to the state of the art, where data is extracted from EHRs and requires extensive cleaning, imputation and labelling by human domain experts, and where there is no means to identify edge cases/failures and consistently turn these into training sets. The result of this is that state of the art methods are ultimately unscalable and prohibitively expensive—and this is greatly limiting innovation and progress in healthcare applied machine learning.

By eliminating the need for a natural language pre-processing step and providing clean, feature-complete data for each training set, embodiments of the present disclosure improve the functioning of various computing systems by improving the processing speed of training and deploying healthcare ML models while reducing memory usage during model training.

Current state of the art in healthcare machine learning requires several pre-processing steps which are compute-intensive and time consuming. The described embodiments reduce the compute needed to achieve good model performance vs. the state of the art, as defined by achieving a given F-score on a given validation set, by (1) removing the need for common state of the art preprocessing steps such as data normalization, NLP feature extraction, imputation and cleaning, and (2) decreasing the number of training epochs needed to reach any given level of performance.

Exemplary technical improvements provided by embodiments of the present disclosure include: improved preprocessing efficient, improved convergence rate, and improved patient outcomes, which are described in detail below.

Improved Preprocessing Efficiency

Data from multiple hospitals and other institutions must be extracted and represented in a single medical ontology (e.g. FHIR) for tokenization and encoding. This conversion step can be broken down further into preparation for feature extraction and tokenization, feature extraction, imputation and cleaning, as described below.

Preparation for feature extraction and tokenization: the extracted data from each institution are in different formats and structures. For example, one hospital may use an EHR such as Epic, exports clinical information as a structured CSV, representing the data in various columns. Institutions with different EHRs will export the data with a different CSV structure which may include different column labels and different content in each column.

As an example, the organization of encounters differ greatly. Some EHRs may export the data organized in hierarchical sets by encounter type: e.g. a set of encounters under a problem code of 'Chronic Kidney Disease' and then another set of encounters under 'Type 2 Diabetes'. Other EHRs export the data organized purely as a time-series.

As another example, the format of encounter content differ greatly. Some EHRs may present encounters as a single column of text. Others may split the free text notes into multiple columns, such as 'Presenting Complaint', 'History', 'Examination', 'Plan' and so forth.

In terms of cost implication, the free text data must be cleaned and normalized into a specific format compatible for the NLP feature extraction task prior to feature extraction (a combination of human and machine steps). As an example, concatenation of separate free text columns in a CSV into a single text blob (e.g. concatenating Presenting Complaint, History, Examination, Plan text columns into a single text blob) may be required. As another example, removal of certain special characters, or removing data points that are blank or have missing fields may be required.

Feature extraction: the standardized data structure, including free text medical notes, must be processed in order to extract features, represented as tokens, prior to vector initialization and embedding for machine learning. Natural language processing (NLP) is often used for this purpose. Human annotators additionally may be used. NLP feature extraction tasks are computationally expensive and time-consuming, as evidenced by the pricing of cloud-based NLP services e.g. Google Cloud NLP, one of the most expensive services available.

Imputation and cleaning: after feature extraction, the resulting set of training examples require imputation and cleaning—as EHR data is often sparse and incomplete due to human error (failure to enter data correctly) and clinical writing style (many physicians use ambiguous acronyms, and most do not record all pertinent negative findings).

In terms of cleaning, training examples from the set which are missing too many features or of poor quality are removed. Commonly, at least part of this process is automated, requiring computation through an ETL pipeline with rule-based algorithms and/or neural networks. This step requires significant computation of millions of training examples. The described embodiments negate the need for such a step by collecting feature-complete training examples as part of patient interactions with the exemplary app user interface; patients are unable to submit requests without answering all the required questions—this means all training examples collected by the exemplary platform are consistently high quality and feature complete.

In terms of imputation, missing features in the training examples are commonly imputed through inference of similar examples, which again requires costly computation. The described embodiments negate the need for such a step by collecting feature-complete information from every patient interaction with the exemplary platform.

Improved Convergence Rate

The described embodiments allow a high performance healthcare machine learning system to be trained and deployed much faster than compared to current state of the art. Fewer training epochs are needed to reach any given level of performance: the described embodiments offer a new mechanism for ensuring training data is always well-balanced with respect to poorly performing edge cases.

It is widely accepted that the vast majority of effort and resource expenditure in machine learning is in the pre-processing of training datasets. It is further widely accepted that a key goal of this pre-processing work is to balance the training data such that poorly performing edge case examples are well represented in the training dataset: this is part of what improves model performance and pushes the model towards convergence to a high F-score.

The described embodiments use real life performance of the production deployed machine learning system to create a closed feedback loop. Mismatch between the output of the machine learning system and the output of a human clinician (their decisions on next steps) constitutes a failure edge case, which is sent to the central servers of the present disclosure. As described herein, these edge cases are classified into sets, then amplified, and incorporated into the training set for the next iteration of the machine learning system. Since edge cases are specifically identified and added to the training set, this is an improvement over the current state of the art, where no such auto-balancing mechanism exists. Current state of the art training sets are comparatively poorly balanced vs. the training sets obtained in the described embodiments, meaning convergence to high performance requires more time and training.

Improved patient outcomes: the described embodiments provide at least two benefits for patients: shorter time to treatment, and better treatment plans. Both of these benefits act to improve well-being and outcomes for patients, including reducing avoidable death. Americans wait an average of 24.1 days for a primary care appointment, based on a 2017 survey of 15 major metropolitan cities (Meritt Hawkins). Since time to treatment is a principal determinant of patient outcome and mortality, the embodiments reduce avoidable patient mortality by reducing time to treatment—the machine learning system can handle any conceivable level of patient load and is not subject to the same supply bottlenecks as the current healthcare system (dependent on the supply of physician-hours, which as discussed, is failing to meet rising levels of patient demand).

Waiting times are long because physician supply is insufficient for the level of patient demand. Most patients who seek medical advice do not have a serious problem, like cancer. If a system could help resolve the simple, low-risk cases a great deal faster, then those patients would get the help they need faster and physician-hours would be freed up for higher-risk cases in greater need of urgent attention and medical care.

For example, for a patient with uncomplicated UTI, instead of waiting weeks for an appointment, they instead use the exemplary app described herein, which takes their medical history and presents it to their doctor within 10 minutes. The doctor, seeing the comprehensive and uncomplicated history, can now safely prescribe trimethoprim within 60 seconds, instead of at a 15-20 minute appointment in 3 weeks time.

As another example, for a patient with a cough, but with red flag symptoms like unintended weight loss and haemoptysis, instead of waiting weeks for an appointment, they use the exemplary app. Within 10 minutes, their doctor is alerted by their dashboard described herein that a patient has presented a high risk cough warranting urgent imaging to rule out sinister causes like carcinoma or TB. They receive the imaging the same day, instead of waiting 3 weeks for the appointment and delaying their cancer treatment. Delay in starting cancer treatment is one of the strongest negative prognostic factors for patient cancer outcomes.

Doctors make mistakes. Medical error is commonly cited as the "third leading cause of death" in the US, or around 250,000 a year. The described embodiments augment human doctors by presenting a complete history with a set of recommendations, acting as advisor to the doctor and making it less likely that they misdiagnose and/or mistreat. Eventually, with proven superiority in patient outcomes F-score vs. human doctors, the described embodiments will give more accurate diagnoses and treatment plans, both of which improve patient outcomes and reduce mortality.

Humans are limited in the amount of data and examples they can ingest, and ultimately as a result, human doctors are forced to take shortcuts in training and inference. This is largely why human doctors make mistakes. Human doctors are taught simple rule-based algorithms in medical school (e.g. 'cough+coughing up blood=possible TB or cancer') and then develop their heuristics throughout training, refining this internal model through seeing patient examples. Unlike human doctors, who may only see 10000s in a career spanning 50 years, the described embodiments can be trained on 100 million examples in a few weeks.

The ceiling of performance for human doctors is fundamentally limited by human bandwidth, but is essentially unlimited for a machine learning system, given enough training examples.

Embodiments of the present disclosure include a way to speed up training set preparation and machine learning training for a healthcare system by more than 20×, and a way to reduce cost per training example more than 10×, while at the same time sourcing only the valuable edge cases likely to improve system performance for the training sets. This is a vast improvement over the state of the art for healthcare machine learning preprocessing (cleaning, imputation, labelling), training and inference.

DESCRIPTION OF THE FIGURES

Embodiments of the present disclosure will now be described in more detail, by way of example, with reference to the accompanying drawings, in which:

FIG. 3 is a schematic diagram illustrating the embedding architecture embodying an aspect of the present disclosure;

FIG. 4 is a schematic diagram of the Transformer architecture embodying an aspect of the present disclosure;

FIG. 5 illustrates an exemplary user interface, in accordance with some embodiments.

FIG. 6 illustrates an exemplary user interface, in accordance with some embodiments.

FIG. 7 illustrates an exemplary user interface, in accordance with some embodiments.

FIG. 8 illustrates an exemplary user interface, in accordance with some embodiments.

DETAILED DESCRIPTION

Figure 1:
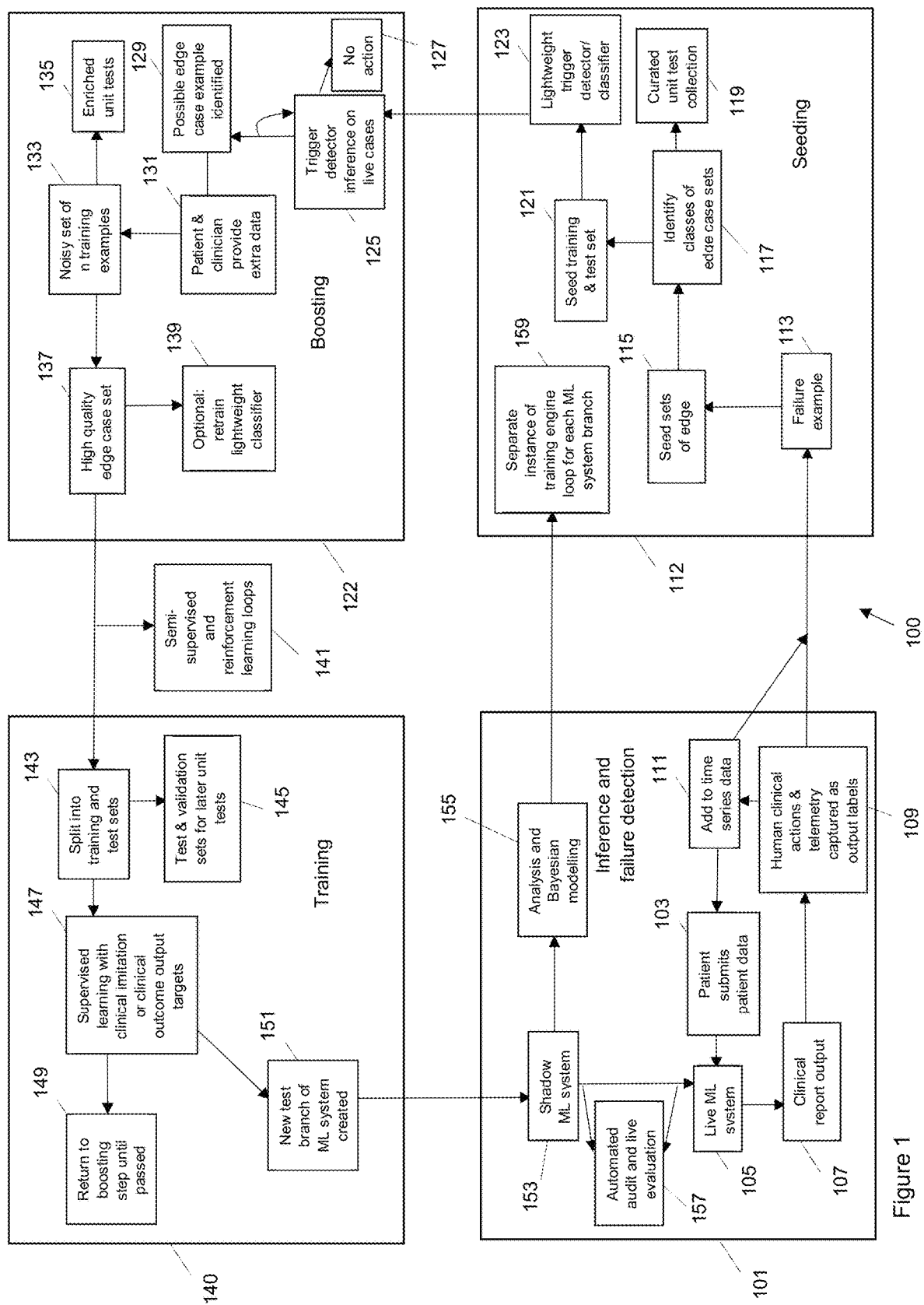
FIG. 1 is a schematic diagram illustrating a method for providing an exemplary healthcare system embodying an aspect of the present disclosure.

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

Healthcare is on an unsustainable trajectory from a combination of demographic change, increased patient expectations and increased per capita chronic disease burden. Globally, health spending is outstripping GDP growth. Patients are having to pay more than they did ten years ago, and are finding it more difficult to access quality healthcare. For example, in the US, health insurance premiums have risen 71% in the past decade. Aside from cost, the supply/demand gap is growing larger. In the US for example, the clinical capacity shortfall is projected to worsen 600% by 2030. In short, there is a finite output of global clinical productivity/per unit time that can be utilised and this is currently insufficient to provide optimal care for all patients. It is also likely that this insufficiency will worsen in future.

Clinical decisions such as diagnosis, treatment or otherwise management of disease is determined through the available information that a clinician knows and understands, whether this be patient reported information, clinical examination, tests, or imaging, for example. The speed and quality of clinical decision making is therefore at least determined in part by the quality of this clinical information and how quickly the clinician can access and process it. Healthcare currently suffers from an information bottleneck, with the notable exception of acute inpatient settings where, conversely, too much information is the problem.

The information bottleneck exists for a number of reasons. Clinicians manually collect the necessary information for clinical decision making through "history taking" (talking with patients) during appointments in their clinics. This process takes up around 75% of the total time of each appointment (so history taking=~8 minutes in the UK and ~15 minutes in the US). This is highly labour-intensive and also problematic for data quality and completeness. In minutes, patients are often required to recall weeks or months of symptoms which may have fluctuated wildly in pattern, severity, and onset, for example, on a daily basis. This results in patchy and unreliable data (for example due to forgetfulness and recall biases). This particular information bottleneck is especially problematic because 90% of clinical decisions (such as diagnosis and management) are made entirely based on patient reported information (the "history") with clinical examination/tests contributing only around 10%.

The manual process of information collection is a rate-limiting step in the provision of healthcare services and severely hinders healthcare scalability and clinical productivity. Information is currently collected manually through appointments, meaning that information is missing in between appointments and outside of appointments and is therefore inaccessible for clinical decision making. Given that the vast majority of a typical patient's journey is outside of healthcare settings, this is suboptimal. This contributes to millions of avoidable deaths a year globally. Without free and complete information flow between appointments, patients get missed.

Efforts have been made to establish a better source of patient data for use in machine learning (ML) systems. For example, some have taken the approach of mining electronic hospital records (EHR). However, practically, these methods just attempt to pick the low hanging fruit within small subdomains of medicine such as acute kidney injury or diabetic retinopathy. This is because it is currently very expensive to label health data and therefore is not a general or scalable solution.

Healthcare data labelling in particular is especially expensive. Most machine learning applications—for example, autonomous driving or general machine vision—do not require domain experts for annotation. For example: in machine vision, the vast majority of the population can correctly point out what a fire hydrant looks like in a picture. As another example, anyone who drives is able to label driving data for autonomous driving training sets. For example, steering the wheel or accelerator/brake patterns provide car control labelling. In contrast, generating health data training sets is particularly expensive and difficult. Providing healthcare and health data labelling is an extremely technical exercise. Only doctors can safely and reliably annotate health data. Doing so requires the given doctor spending time to interpret complex clinical information in order to synthesize a clinical decision or conclusion, which costs money. In addition, making the correct clinical decision is rarely so straightforward or obvious that it can be done in seconds. For example, to generate one training example for managing asthma, a relatively straightforward condition, the doctor must still read through and process significant amounts of complex information, usually at least half an A4 page, and then abstract this into a clinical decision output. This usually takes at least a couple of minutes (compare this to someone spotting a fire hydrant in a picture).

Thus, in having to pay doctors to label data, these two factors combined (hourly cost×unit task time) currently create very unfavorable unit economics for scaled machine learning. Ophthalmologists have been paid over $25 million to label cases of diabetic retinopathy in retinal image scans. Not only is this particular case much faster and more straightforward than labelling time series data, but this is just for a narrow application in a single subspecialty of medicine.

Another approach to acquiring labelled training data might be to use existing patient healthcare data locked in electronic medical record software used by hospitals and clinics to record notes. This approach includes the use of standard resources like Fast Healthcare Interoperability Resources (FHIR) to pre-train a model as much as possible, and then aggregate a few different sets of EHR data. Natural Language Processing (NLP) is then used to extract features and train the model. Cross-validation must then take place on a different EHR set, which requires signing new contracts with a new institution, potentially seeking retrospective consent, and then carrying out further mining and labelling. This approach is not viable for developing a general healthcare AI (managing any presentation from anyone) for several reasons. Firstly, widespread application of machine learning is a relatively new phenomenon, so historically patients were never consented for these datasets to be used for third party machine learning training. The cost of the retrospective consent exercise itself vastly outweighs any potential cost savings of using pre-existing datasets. As a result, only a tiny subset of EHR datasets are actually available for ML use. Secondly, EHR data is highly irregularly spaced across time (for example, dependent on hospital admission) with most patients having only one or two time series points (as most people who enter hospital do not do so very frequently), leading to data insufficiency. Lastly, EHR data is extremely biased and poorly representative of the overall patient population. Generally, patients only enter hospital when they are relatively sick and at high risk. 90% of healthcare demand is dealt with at the primary care level; only around 10% of healthcare demand trickles down to secondary care level or further downstream. Neural networks trained on this data therefore will never generalize to the general population and would be greatly skewed towards overmedicalisation if applied to general population healthcare, including proposing unnecessary tests, scans, or treatments as it was trained on a set of very sick patients. The datasets are further unbalanced by geographical differences in demography and phenotypes, whereby a small number of EHR datasets sourced from particular geographies do not accurately model the general population of patients nationwide or worldwide.

Data quality, insufficiency and lack of a scalable means of data acquisition and preprocessing are currently key limiting factors preventing wider application of machine learning systems to healthcare data. No matter how good algorithms and hardware are, an ML system requires real world context in order to output useful results. An algorithm is only as good as the inputs it is trained or optimized on. The performance of a deep learning system is strongly dependent on the quantity and quality of training data used to train it. The current state of the art methodology is therefore only suitable for narrow domain applications within secondary care, and could only ever generalize to the secondary care patient population. This is largely why products in this space have been limited to very narrow subdomains of medicine, often performing reasonably straightforward binary classification tasks on imaging only (predicting diabetic retinopathy from retinal scans, detecting lung cancer from CXRs).

Existing systems and methods also lack in particular the ability to quickly and cost-effectively identify edge cases. That is, cases which have a low probability of occurring. In healthcare, these also tend to be cases where the patient is at particularly high risk and where it is most important to correctly identify the diagnosis and proper management.

Figure 2A:
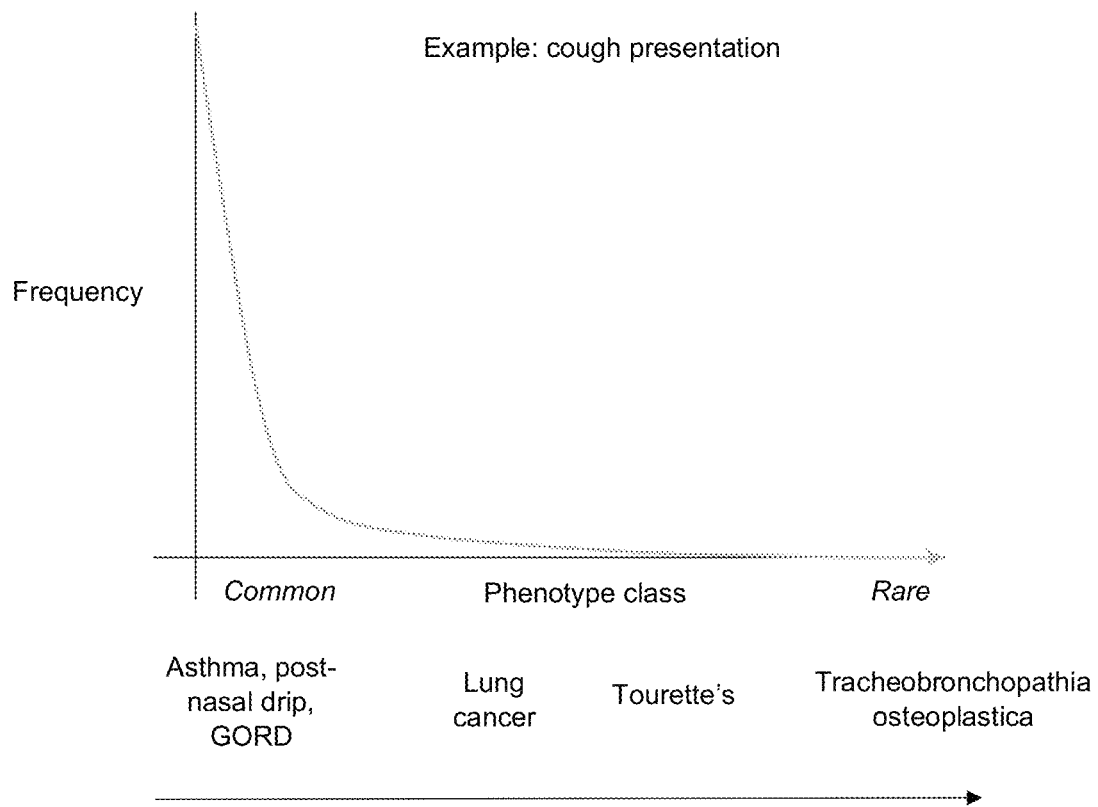
FIG. 2A is a graph illustrating an example of frequency of phenotypes for a given symptom.
Figure 2B:
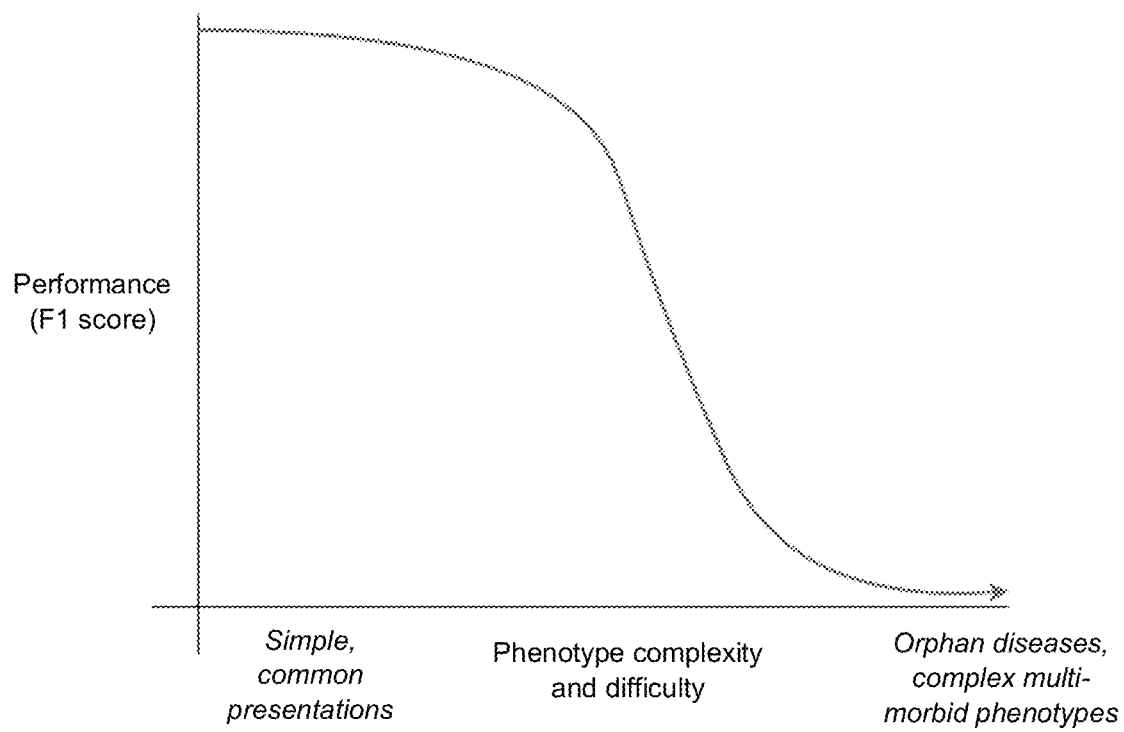
FIG. 2B is a graph illustrating clinical performance as a function of phenotype complexity and difficulty.

FIGS. 2A-B and the accompanying description outline why it is critical that edge cases be specifically identified and incorporated into training sets for the healthcare system and machine learning system to perform well. FIG. 2A illustrates a graph showing frequency of a condition as a function of phenotype class. Clinical phenotypes for any given set of symptoms and patient states follow a power-law distribution with a long tail. The long tail indicates the large number of edge cases which may exist, highlighting the importance of being able to identify these edge cases. The graph illustrates the presentation of a cough as an example. As we progress across the tail along the X axis, phenotypes generally become more complex and are harder to diagnose and manage.

FIG. 2B illustrates a graph showing the performance (and particularly the F1 score) as a function of phenotype complexity and difficulty. Human clinical performance falls as case complexity and difficulty increases. At the lower end of complexity and difficulty (simple and common presentations), have well-established, rule-based management protocols and are essential clinical knowledge in textbooks. At the higher end of complexity and difficulty, there is no established management paradigm, and clinicians have little to no accessible information. Information concerning such cases is mostly limited to literature and cutting edge research.

Figure 2C:
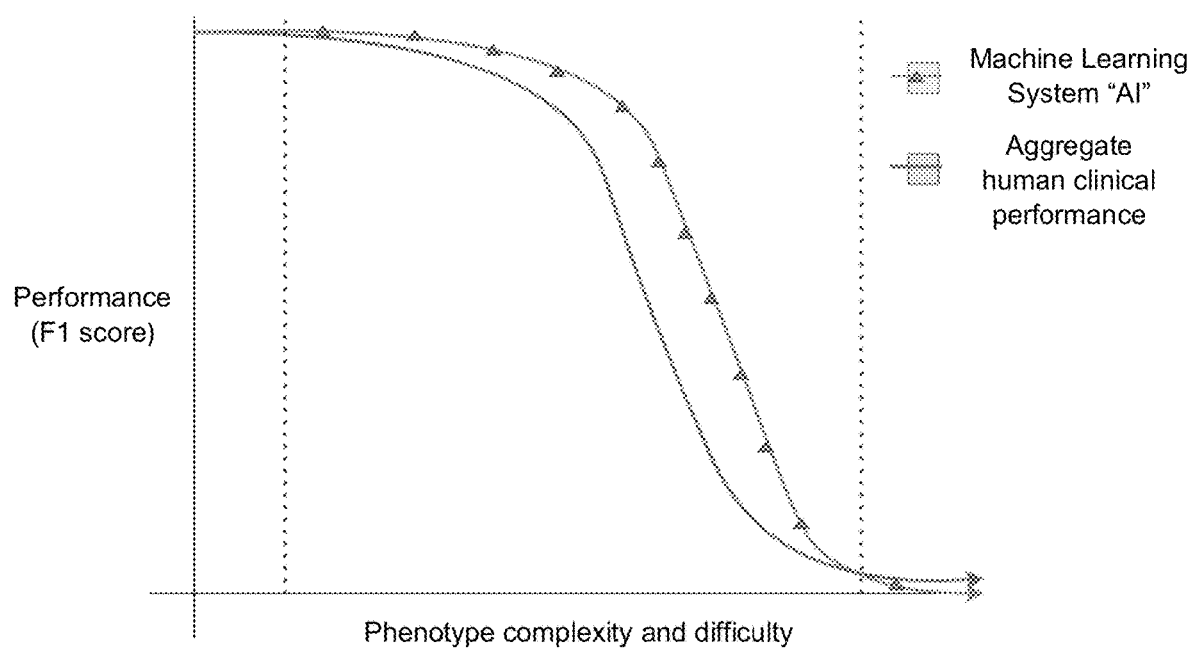
FIG. 2C is a graph comparing human clinical performance against the performance of the machine learning system embodying an aspect of the present disclosure.

FIG. 2C illustrates a graph showing performance (in particular F1 score) as a function of phenotype complexity and difficulty similarly to FIG. 2B, but with comparison of performance of the machine learning system and aggregate human clinical performance. In a high data scenario (where a good amount of data can be sourced), the machine learning system is likely to outperform human clinicians in less common, feature-rich scenarios as long as sufficient training data is available and the data is of a high quality.

When applying the machine learning system to edge cases in the long tail of the graphs above, it becomes increasingly important to optimize for as low a false negative rate as possible for serious conditions. An autonomous system should err on the side of caution and refer risky patients to humans, and should have a false negative rate better than that of the average human clinician. Table 1 below shows an example of prediction rates.

TABLE 1

|  | Predicted: No | Predicted: Yes |  |
|---|---|---|---|
| Actual: No | True Negative = 50 | False Positive = 10 | 60 |
| Actual: Yes | False Negative = 5 | True Positive = 100 | 105 |
|  | 55 | 110 |  |

A common way of measuring performance is the AUC of the model, where 0 represents the model predictions being 100% wrong and 1 represents predictions being 100% correct, regardless of what classification thresholds are used. It is reasonably trivial to create simple policy based analytic models that achieve an AUC of 0.7-0.8 for specific phenotype domains or presentations (for example, a patient present with cough). As discussed, this is because a small number of diagnoses account for a very large proportion of the presentation phenotype—by simply classifying cases into "asthma", "post nasal drip" and "GORD" and completely ignoring other causes, one may quite easily build a model that is around 70-80% correct using simple rules. However, this is not very desirable or useful, as this model would be plainly incorrect when it matters the most! The only feasible way to create a model that can handle any presentation and context is through a trained machine learning (in our case, deep learning) model.

Improving a healthcare machine learning system above AUC 0.8, to say, 0.97, for any possible patient presentation and context, is widely regarded as very difficult. The major barrier is that more training examples of the same common conditions do not improve system performance; indeed, this would reduce performance for correctly predicting minority classes. What is needed is specific training examples for the long tail of edge cases, especially where the system has failed to generate the correct outputs or otherwise underperformed. There is currently no repeatable and scalable means to identify and acquire training examples for these edge cases.

For a useful and time saving machine learning system, the model may have a better F1 score across the full tail distribution of presentations when compared to at least the average clinician, and it may at the same time have a lower false negative rate across the full distribution when compared to at least the average clinician. Achieving this means spending the vast majority of effort and time dedicated to increasing performance for the tail end of phenotype classes: the edge cases.

It is currently difficult to source high quality edge cases quickly and cost-effectively, and we have tried to establish that identifying and sourcing edge cases is important for providing an effective healthcare system and machine learning system. Not only is sampling more of the same sorts of common diagnoses not particularly helpful for improving the performance of any given healthcare AI neural network, but unbalanced data is actively harmful. It skews misclassification costs towards the majority classes (which typically include common diagnoses) making it more likely that the neural network simply chooses the majority class, even when it shouldn't. This is particularly harmful in healthcare, as the rarer the class, the more serious the condition tends to be and the higher the cost of a false negative for that class. For example, misdiagnosing a common cold as something else vs. misdiagnosing brain cancer as something else.

In order to provide an effective healthcare system that is applicable in the majority of circumstances, data collection must be improved. The data collection needs to be as near feature-complete as possible in order to generate high quality training data that is also feature-complete: that is, all the relevant input information for differentiating a given diagnosis and management decision. Consultation notes are a second derivative of the real inputs from patients and are therefore sparse and incomplete. Feature complete information is what creates the necessary structure in data to allow humans and/or a machine learning system to discern the correct set of differential diagnoses from a given presentation. An illustrative example is as follows: imagine two patients, patient A and patient B. If all that is known about patient A and B is that both have a "cough of 4 weeks", it is impossible to synthesize an accurate diagnosis or management plan. If, hypothetically, patient A has asthma and patient B has lung cancer, it is impossible to differentiate between these diagnoses based on the available feature information. Any machine learning system therefore needs to receive feature complete input, as human clinicians do when they take a detailed history, in order to perform well and to find meaningful structure in different clinical cases. Greater information flow and automation is likely to greatly benefit both sides of the healthcare market.

There are currently no granular efforts towards an autonomous general healthcare AI system. To summarize, the current state of the art in healthcare ML training & inference is strongly rate limited by the (1) lack of a scalable means of acquiring high-quality, feature complete healthcare data across the full spectrum of conditions and contexts that a patient may present with, (2) lack of a scalable means of preprocessing (aggregating, cleaning, labelling, encoding, imputing) this data into machine learning training sets without prohibitive labour and compute costs, and (3) lack of a scalable means of balancing training data sets with the appropriate mix of examples, and favouring edge case failures.

An example method for providing a healthcare system, and a healthcare system, will now be described with reference to FIGS. 1 to 4.

FIG. 1 illustrates a healthcare system 100, and particularly illustrates a method for providing the healthcare system 100. The method can be considered to comprise four main steps. These include: inference and failure detection 101, selecting or seeding 112, boosting 122, and training 140. Each of these will be described in more detail below.

The method may begin at step 103 with a plurality of patients inputting patient data into the healthcare platform. In this example, a patient may input new medical problems via their electronic devices through the healthcare platform web application on a networked computing device. For new problems, patients may first be asked to enter in their top level symptoms for a given service instance: for example "back pain" or "cough" or "fever". This then loads a corresponding set of DAG templates (directed acyclic graphs). Directed acyclic graphs are well known, and are graph representations of data described through nodes and edges. Each DAG template can be thought of as the superset of questions specific to that symptom or presentation (e.g. a cough DAG clinical module) which contain all the necessary structured questions to generate a feature-complete data point for both the human clinician and the machine learning system to properly differentiate the diagnosis and hone in on the correct next management steps (e.g. dry cough, 6/10 severity, worse at night, exacerbated by cold and exercise, X social history, Y family history and so forth). Such DAGs are also a graphical representation of question flow control in which the properties of nodes and edges are used to calculate the next question node, and in doing so, allows us to ask questions contextually—skipping over irrelevant questions or alternatively adding in new sets of specific, targeted questions. For example, a patient in which we have calculated a QRISK2 score of >20% is considered at very high risk for cardiovascular events such as stroke and heart attack, and in this circumstance the DAG would ask a further set of much more detailed questions elucidating further lifestyle risk factors, adherence, family history and so forth e.g. "How often do you exercise? What does the exercise typically involve? Have you ever discussed taking statins with your doctor?" Such questions may only be relevant in certain circumstances, and by contextualizing the question flow, we are able to deliver fully personalized reviews that may be completed rapidly for low risk patients, and signed off rapidly by the clinicians who receive these reports through the web app dashboard we offer. On the other hand, patients at appreciable risk may receive much more comprehensive history taking to further elucidate risk factors. For on-going or chronic problems, for example asthma or type 2 diabetes, patients are prompted to complete reviews autonomously, as a way to track disease control and risk of adverse consequences such as hospital admission. The healthcare platform also receives telemetry data used to inform derivative variables such as patient adherence.

A healthcare data platform may receive one or more patient inputs comprising patient data from the one or more patients in response to one or more patient questions and/or the healthcare platform may receive one or more telemetry inputs comprising patient data; and the patient data may be obtained by the machine learning system through the healthcare data platform. This provides automated collection of patient data which is feature complete and has a very high signal to noise ratio, and can be directly encoded unambiguously into training data. The healthcare platform may be a software platform. The machine learning system may obtain the patient data from the software platform. The one or more patients may comprise any user capable of inputting information relating to the one or more patients and do not necessarily need to be the patient themselves. For example, a caregiver may input patient information for a patient in response to one or more patient questions.

By automating the collection and interpretation of this data, and collecting this regularly at appropriate intervals through the healthcare platform, significant clinical time and productivity headroom can be freed up. High risk patients may be autonomously flagged by the healthcare system and are seen earlier and managed more intensively as a result. Such a workflow makes healthcare much more scalable—as mentioned earlier, information gathering is the most time consuming aspect of the current healthcare workflow. It would also allow healthcare to be agile. That is, clinical decisions become two-way doors because information is updated regularly through the healthcare platform, meaning the data is complete across time and is always accessible. High-risk patients may be identified in real time by the machine learning system, allowing them to be treated before they deteriorate to an ED admission, or die. Hospital admissions cost around thirty times more than a primary care appointment, so proactive and early management of patients reduces demand burden. Treatment regimens can be optimized on the timescale of days or even hours rather than appointment to appointment which can often be weeks or months apart. This agility saves money, time and lives.

The healthcare software platform from which the machine learning system may obtain the patient data relating to the one or more patients may be accessible through any suitable computing device. For example, the healthcare platform may be accessible through a networked computing device such as a smartphone, tablet, or computer device such as a personal computer or laptop running the healthcare platform software. The computing device may also comprise a user input enabling a user such as a patient or a clinician to input patient inputs.

The method may comprise the machine learning system: determining a plurality of predictions based on the patient data; receiving, from a user, a plurality of user inputs labelling each of the plurality of predictions as a success or a failure; and generating training data based on the labelled patient data and the plurality of user inputs. In other words, the machine learning system may receive data and form a plurality of predictions, all of which are assessed by a user such as a clinician to establish whether the predictions are successes or failures. That is, the healthcare system and machine learning system are capable of dealing with a plurality of users or patients, and indeed a large number of users or patients.

Importantly, this patient data is pre-structured and mostly categorical or ordinal, with explicit relationships denoted by node connectivity and their edge properties. These DAG templates may be dynamically generated according to certain outputs of the machine learning system. These question DAGs may be expert systems constructed by human experts with domain knowledge, or they may be fully automated and dynamically generated from knowledge graphs constructed using the outputs of a part of the machine learning system (a generative transformer which outputs constrained text sequences), and therefore may not require human input to construct or maintain. This ensures that the data is high quality and has a high signal to noise ratio. Crucially, this means an NLP pass is not strictly necessary for extracting features—NLP is a particularly lossy step in healthcare ML applications. Furthermore, the pre-structured features in themselves contain sufficient structure for the machine learning system (or indeed, a human clinician) to generate the right outputs.

The primary data source is from the healthcare platform provided to patients and clinicians for digital healthcare provision, however external datasets may also be used. When external datasets are used, the data is mapped onto the system's ontology. That is, to the input vector language that the machine learning system has been trained on and understands. The external datasets are not necessary for the technical advantages described, but are nevertheless an advantageous integration. The healthcare platform may expand to offer services beyond primary care, and provide services to community care, secondary and tertiary care and obtain data of various modalities. The platform may also integrate with third party data sources, for example, omics sequencing companies, IoT or medical device data.

At least some of the patient data may be directly bucketized and tokenized into a standard medical ontology, particularly pre-structured data collected by the platform. Bucketizing serves a dual purpose: (1) compressing ordinal and interval scales (e.g. age) into smaller number of token representations, thereby reducing the feature space and helping the system learn faster and reducing the likelihood of overfitting; and (2) helping fully anonymize data (e.g. 63 years old becomes 4850, a token representing the 60-70 age range). The patient data, including the structured data, may be mapped to a consistent medical ontology which may include FHIR, ICD, SNOMED-CT, or any suitable ontology.

For structured data from external integrations, there may be an extra mapping step, which translates the external datasets into a consistent ontology which is used to encode input tokens from which learned embeddings can be derived. In this scenario, the FHIR or International Classification of Diseases (ICD) standardized medical ontology or the like may be used, mapping both the healthcare platform data and external data onto it, thus standardizing conceptual representation before encoding into input vectors.

Data, particularly from external sources, often cannot be directly encoded or mapped unambiguously. In order for this data to be considered in combination with structured data from the healthcare platform, the unorganized/unstructured data requires transformation to the same medical token ontology as the one used by the healthcare platform data. The method may further comprise the machine learning system: using an ensemble of neural networks to fuse multimodal inputs (such as video, free text, or sequencing data) of patient data into a singular shared token ontology comprising one or more tokens and converting the one or more tokens to one or more continuous vector representations; and/or representing at least some of the multimodal patient data as latent space embeddings which may be fed directly into the neural network layer downstream. In some embodiments, a stacked ensemble architecture is employed with an initial fusion layer in which three base models may be pre-trained and learn useful representations for different data types. Their outputs may be fed into the core Transformer network downstream, represented either as reserved tokens (only used by the multimodal ensemble or as latent space embeddings). For example, for free text, a BART-like denoising autoencoder (a variant of a transformer) may be pre-trained on labelled domain data for summarizing text, compressing very long sequences of audio transcripts or virtual consultation text into much smaller sequences of tokens (representing relevant features), or a series of vectors with dimensionality equal to the fixed length embedding size of the core transformer (latent space embeddings).

Taking a case of asthma as an example, patients using the healthcare system with active asthma may complete a review about every 2 weeks. Initially, the patient is provided with one or more high-level screening questions based on the clinically validated Royal College of Physicians (RCP) 3 scoring tool through the healthcare platform. To illustrate, one of the RCP3 questions is: "In the past 2 weeks, have you had your usual asthma symptoms during the day (cough, wheeze, chest tightness or breathlessness)?" If a patient answers yes to this, the patient may be taken through a further subset of questions to explore each symptom, which may include severity, onset, and pattern, for example, using the same schema as the gold standard, applied by a human doctor as a ground truth (e.g. exploring a pain symptom according to the Site, Onset, Character, Radiation, Associations, Time course, Exacerbating/relieving factors, Severity (SOCRATES) mnemonic).

Whilst as explained, though some of the data may be externally sourced and cannot be directly encoded unambiguously, the vast majority of data collected (such as more than 90%) may therefore be structured and constitutes pre-labelled features that are known to be relevant for arriving at the correct conclusions for the given case presentation. Collecting and explicitly screening for known features is critical to supervised machine learning in healthcare, as this reduces the otherwise huge search space and dimensionality for associating inputs to outputs, a particular problem in healthcare. There is an inordinate amount of trivial and irrelevant information.

Preprocessing is a necessary prerequisite of machine learning system inference. This is described in detail through FIG. 3 and the accompanying description: the preprocessing steps for training set preparation and inference are analogous. To summarize here, each encoded feature collected by the healthcare platform through clinical DAGs is mapped to a standardized medical token ontology ("tokenization"), with each token becoming embedded as a learned vector representation in the core Transformer block (in one embodiment, a BERT or Reformer) of the machine learning system. The sequence of tokens, forming a token sentence, may span across multiple time points and data types and receive metadata labels through the addition of special reserved tokens to the sequence. Previous data points belonging to the patient from earlier instances of usage of the healthcare platform may be concatenated onto the token sentence. Step 105 represents inference—the data input is transformed into a plurality of predictions and recommendations by the machine learning system. The outputs are combined with an explicitly engineered rule-based policy system based on medical domain knowledge. At step 107, the machine learning system and policy system together produces outputs in the form of clinical reports comprising the plurality of predictions, recommendations and a processed version of the patient history taken by the DAG, and is sent as JSON objects to the web/mobile app dashboard for viewing by the clinical team on their user computing device. The report also contains the top differential diagnoses considered by the machine learning system, and the contributing reasons to each (through attention mechanisms outlined in the accompanying description of FIG. 4, in step 143).

The method may further comprise the machine learning system providing an output to a user. The output may be provided through the healthcare platform. The output may be a clinical report. The user, such as a clinician, may receive the output through the healthcare platform. The clinician may receive an abstracted and presentation friendly version of the clinical report generated from patient data collected from the patient. The clinician may interact with the output through a web or mobile app dashboard. The clinician may then act on the basis of that information using remote management tools through the healthcare platform or through their own means, for example, in prescribing treatment, making a diagnosis, creating a care plan, reassuring the patient, book an e-/video consult, an in-person appointment, asking for further information or any suitable action.

Between steps 107 and 109, the clinician reviews the report containing a plurality of predictions, recommendations and processed patient information made by the machine learning system, and uses the clinical report to decide on appropriate management steps—whether this be issuing a prescription, asking for more information, booking an investigation or a virtual or physical appointment. The clinician clicks a "Manage" button, which opens a pop-up in the web app. The pop-up is pre-populated with what the machine learning system believes to be the appropriate actions to take—e.g. "prescribe omeprazole" or "book urgent head CT within 2/52" or "book physical appointment and examination within 2/52". The clinician may de-select any number of these suggested actions or predictions (for example, the differential diagnosis), edit them or add completely new actions or predictions not suggested by the machine learning system. All actions are structured and are categorical and/or ordinal in nature, and unambiguous, such that they can be reliably and directly encoded in a consistent manner without further interpretation, and then mapped onto a consistent medical token ontology used by the machine learning system (described in the later step 143). In such a way, the clinician provides an input to the healthcare platform labelling each of the predictions as a success or a failure. It will be appreciated that the lack of a prediction or recommendation from the machine learning system can similarly be a failure, for example, if the human clinician needs to add an additional action to the list of next steps. In this way, clinical management of patients through the platform provides valuable target feedback ("output labels") for training the machine learning system—a common analogy is that the human clinicians are teaching the machine learning system through example (millions of examples). In this example, the clinician's input is established as a ground truth. It will be appreciated, however, that a clinical outcome may equally be established as a ground truth.

The interaction with the user such as the clinician then takes the process back to the beginning of the loop on the provision of healthcare. That is, the patient is informed via the patient output of any action required, such as a medication change to pick up, an appointment, or being asked to agree to a care plan, to give some examples. If their active problem is not yet resolved, or is a chronic disease, they may continue to be monitored at an appropriate interval through the healthcare platform which may prompt a patient for further information, such as by asking questions and checking in on them at appropriate intervals. This therefore continues generating time series data, advantageously producing consistent, structured data. The clinical dataset (actions, inactions, any other data recorded including metadata) may be concatenated to the pseudo-anonymized training example relating to that particular clinical report. Clinician-side actions, data and metadata may be used to estimate feature/token weight in various contexts and this may be used to train the Bayesian skip-gram model that initializes tokens into learned embeddings.

There is typically a lot of noise in patient submitted information: there are critical bits of information hidden among a large number of trivial facts and padding words in any given presentation. Furthermore, the importance of each information bit is greatly affected by the surrounding context. An identical bit can represent vastly different meanings: for example, the importance of a given symptom is greatly affected by the pattern of other symptoms and the biopsychosocial context of the presentation. Sharp pleuritic pain in a 60 year old construction worker exposed to asbestos has a completely different aetiology to sharp pleuritic pain in a young patient who fell off their bike. Therefore an identical token, representing a specific symptom, can have several different meanings depending on context. Another example: a "chronic cough" is not very important information for someone with asthma, whereas "shivers" is very important. On the other hand, a chronic cough can be a very important piece of information in someone with unintended weight loss. By seeking feedback from clinicians on key areas of concern as they take action through our platform, and aggregating these human attention scores, we can train the Bayesian skip-gram embedding model used for first initializing token sentences, to represent these different semantic meanings, and their likelihoods, as posterior probability distributions. This imparts additional latent context information onto embeddings; intuitively, this means token/semantic context is already partly reflected in the initial word embeddings' vector space. This significantly lowers the training data requirements for the neural network achieving a given level of performance, meaning it can be trained faster, and more cheaply.

The clinician's actions and management proposals are communicated and agreed with the patients, through relaying the suggested management plan to a network computing device used by the patients. At step 111, the data associated with the clinical case, including clinical actions are added to the time series data associated with the patient in the cloud. The time series data is used as both a confidential longitudinal record for each specific patient and their associated medical professionals, and as the substrate for constructing training examples for the machine learning system through an anonymization and tokenization process (described in Step 143). The time series data includes information on the machine learning system's inference outputs and also actions taken by the human clinician. This data allows the level of disagreement to be quantified through cross-entropy loss, across multiple points in time.

Embodiments of the present disclosure include methods to detect failure or poor/unacceptable performance in healthcare neural networks in a fully autonomous way in real time.

The method may comprise using one or more user inputs of the plurality of user inputs labelling predictions as successes or failures to evaluate the performance of the machine learning system and determining whether or not regression of performance has taken place.

Where the clinician disagrees with a recommendation or prediction of the machine learning system, a potential failure of the machine learning system has occurred. Bayesian proxies for failure are also used to determine potential failure cases, by selecting cases at the tail end of the distribution: for example, if a given datapoint is a high outlier in terms of the uncertainty of the machine learning system's predictions (expressed as softmax distributions). Even if a given system output fully agrees with the human clinician, if the underlying softmax is very uniformly distributed across a given number of classes, the machine learning was very uncertain which of those classes represented ground truth and could easily have been "tipped" into one of the other (incorrect) classes—such instances may enter into the failure pipeline assumed to be failures, or may first be examined by a domain expert: does the domain expert believe the system is right to be as uncertain as it is in the given context? Why might the system have been so uncertain? Similarly, the Bayesian lateness of a prediction as compared to human performance can be used to proxy machine learning system performance. Regardless of how the failure is detected, the time series data for the patient is processed into a failure example for the machine learning system and stored in a database of failure examples: this involves concatenating the data on the ground truth outputs e.g. clinical actions, and then bucketizing and tokenizing the data into token sentences.

The healthcare platform and machine learning system analyses and generates predictions for a plurality of patients, generating a plurality of predictions, all of which are assessed and labelled by a clinician as successes or failures.

At step 113, the machine learning system establishes a failure example. Generally, these failures can be thought of as edge cases. Each edge case failure is organized and added into a very large array of failure examples, after anonymization and tokenization into training data. Such failure examples may span across the entire spectrum of healthcare: for example (1) a failure to diagnose the correct condition from a cough presentation and associated symptoms (2) a failure to suggest an urgent abdominal CT in response to a jaundiced patient in a given context (3) suggesting the wrong medication (4) failing to ask a certain follow-up question in response to a patient with anemia and who has a history of heavy metal exposure. In order to empirically track performance of the machine learning system in a modular and task-specific manner, it is necessary to bound failures within defined properties, thus clearly defining separate edge case classes. For example, one schema for this could be explicitly defined by a human domain expert purely on the ground truth diagnosis of the patient: how well is the system performing for detecting and managing lung cancer? In such a way, the large array of failure examples become grouped by their edge case class and all share the class' defined properties, allowing for fair future comparison. This makes it far easier to unit test and track performance changes across time and across different failure class domains. The examples within each failure class, having been anonymized and tokenized, are constructed into seed training and test sets represented by step 115 and step 117. A fully automated alternative to explicitly defining a failure class, is to cluster the array of failure examples in an unsupervised manner. First, the failure examples are transformed by a denoising autoencoder, pre-trained to reconstruct domain-specific token ontology (through forced compression through a sparse hidden layer) and pre-trained to output the most relevant tokens for the final blender/integrator of the machine learning system. This auto-encoder reduces the dimensionality of the failure examples and improves clustering performance. The reduced dimensionality latent embeddings are then processed through an unsupervised clustering algorithm, for example, hierarchical agglomerative clustering. The clusters may automatically be defined as separate failure classes and passed into step 119 and 121. At step 119, the edge case classes are interpreted and stored for later unit tests. The aim of step 121 and 123 is to train a lightweight binary classifier for each of the plurality of failure classes. A suitable method is through support vector machines, though there are other suitable methods. Each binary classifier, specifically a support vector machine, is trained to discriminate whether a given inference example belongs to its edge case class or doesn't belong to its class. This step is necessary for generalizing the training architecture to handle optimization problems in a scalable way and is required for full automation of the training architecture. As the system improves, the modalities of failure become increasingly obscure and non-obvious. For example, a large group of failures may share the commonality of some latent state or variable of the machine learning system (hidden and broadly inaccessible to human interpretation) rather than an obvious input or output feature. This makes it very challenging, if not impossible, for humans to identify the commonality. In these circumstances, a far more scalable way to add more examples of many different edge case classes from the network is to use autoencoders, unsupervised clustering and training binary classifiers for each cluster of the seed failure examples, rather than attempting to engineer an explicit rule-based solution.

At the boosting stage of the training architecture, 122, the seed-trained classifiers are used to boost the small edge case failure set used to train the classifiers themselves, with more examples belonging to the edge case class from the user network (whether or not failure actually occurs in the instances). Such classifiers may be modulated and gated by rule-based policy systems or "criteria" in order to reduce compute or improve discriminatory power—a simple example is to automatically rule out any cases where the patient is female, where the edge case class relates to prostate cancer. Together, the binary classifier and policy system therefore form a detector system. At step 125, detector inference is triggered on live cases, using an intermediate feedforward layer output of the machine learning system as input. Where the conditions of the policy system are not met or where the binary classifier score is subthreshold, no action is taken (step 127). The system does not believe the case to be an example belonging to the edge case set of interest. Where the conditions of the policy system are met and the classifier score is above the predetermined threshold, a possible edge case example is identified (step 129). Continuous inference on live cases across time generates an increasing number of further edge case examples. The detector may be run on either local user computing devices or on a cloud computing service, and may remain deployed and active until a suitable number of examples is generated. At step 131, for identified edge case examples, the detector system triggers requests back to clients, in this example, to both the involved patient and the clinician for more information. The classifier does so by triggering a DAG associated with the boosting step for the particular edge case failure class, which is interpreted by a server and presents questions and gathers data via the healthcare platform (web or mobile app) running on local user computing devices. By seeking this further information, the classifier improves the quality of the data and therefore the edge case examples that will make up the training set for the machine learning system, collecting a wider array of features than normal. This increases the chances of finding meaningful structure in the data that may allow the machine learning system to improve its performance in the edge case class in future inference. Utmost care would be taken to ensure this is done in a sensitive way. That is, after confirmation from the clinician that any potential bad news has been broken to the patient, and subject to full informed consent of both patient and clinician. Therefore, based on the output of the classifiers, the healthcare platform server may at that point immediately take further contextual actions, for example, asking specific extra questions to the patient via the healthcare platform, asking the patient to take a certain action via the healthcare platform, extracting certain metadata or sensor data, to give some non-exhaustive examples. The healthcare platform may also store a task(s) in local devices or in a server memory to execute later. The plurality of examples collected by the detector system of the boosting process is aggregated into a noisy set of training examples for the given edge case class, represented by step 133. These training examples may be subject to further human interpretation and curation by domain experts, who may manually clean and discard members of the set. Alternatively/in addition, the noisy training examples may also be de-noised in an unsupervised manner using a denoising autoencoder and an associated policy system—for example, discarding training examples with fewer than X time series data points and at step 137 a high quality set of edge cases is provided. Optionally, at step 139, the classifier can be retrained at this stage using the cleaned set to improve its discriminatory performance and improve signal-to-noise for further captured examples.

Specific, underrepresented demographic traits may be oversampled on purpose, through trigger conditions tuned to weigh certain demographic parameters more highly. This helps counteract the effect of input biases that may skew system performance towards certain groups such as to, for example, prevent the system performing better on wealthier individuals who are more adherent to using the healthcare platform compared with lower socioeconomic status groups.

This technique can rapidly and precisely generate further training examples for identified edge cases at unprecedented quality and magnitude in comparison to existing methods, for example, EHR data mining. For example, although only 0.1% of coughs turn out to be lung cancer, this still translates to about 48,000 cases per year in the UK, or around 130 per day for a population of 67 million. A training set in the low hundreds may be sufficient for the machine learning system to reach human-level performance in suspecting lung cancer and taking appropriate steps. Furthermore, as this training data may be acquired from a wide geographical net with targeted oversampling of underrepresented groups, the sample set is more likely to be representative of the general population and therefore generalize well to future unseen examples in an equitable manner.

At step 141, the edge case set is provided to a semi-supervised reinforcement learning loop. This has a similar training architecture as described below but with different output targets and a different training process. Between steps 137 and 143, the edge case set enters a supervised training pathway in order to train the machine learning system at scale using high quality labelled examples of the edge case class, where the system had previously underperformed.

At step 143, the training set prepared through the boosting stage is separated into training and test sets. In this example, the test set is between 10 and 20% of the total cases, and at step 145, the test set is used for validating the performance of the machine learning system after receiving training for the failure class. Between steps 143 and 147, the machine learning system is trained through supervised learning, which will be explained in extensive detail below with reference to FIG. 3 and FIG. 4.

FIG. 3 illustrates a flow diagram of the embedding architecture applied in the machine learning system. In this preferred embodiment, the core stack of the machine learning system is a Reformer or BERT (step 319) which accepts a sequence of embedding vectors of fixed dimensionality, generated from a sequence of tokens of any length as the initial input. A complete token sequence is a single training example used to train the machine learning system. The tokens are derived from a number of different sources: in this example, the key tokens are from structured data entries generated by the healthcare platform. Tokens may also non-exhaustively come from other multimodal input sources, for example, upstream neural networks in the fusion layer of the machine learning system which process multi-omics, visual and free text data, generating a sequence of tokens representing relevant features (steps 307 and 309); alternatively they pass latent space embeddings directly into a layer in the core Transformer stack. Any number of time series data points and any combination of input sources may be used to generate the token sequence, meaning that token sequences may span across multiple interactions with the healthcare platform and multiple time points in the patient's history, and from multiple data sources (steps 303 and 305).

Different models are used for the multi-modal fusion layer of the machine learning architecture. Video and imaging benefit from a different model architecture than structured, tokenized information, namely a form of convolution neural network (CNN) and Semantic Segmentation, which is especially robust for extracting features from images. Similarly, the model may be pre-trained to extract key features relevant for the machine learning's prediction, such as clinical prediction tasks, representing these as either reserved token sequences or vector embeddings. Similarly, multi-omics data benefits from a Graph Network Transformer approach. This may also output either reserved token sequences or vector embeddings.

The primary data source is in structured format generated from data collected by the healthcare platform (step 301). The data is stored as matrices of mixed types (strings and ints) and indexed according to a standard schema ontology that is shared with a rule-based decoder. The rule-based decoder is thus able to translate and map these matrices into a sequence of unique strings (step 311). The strings are then converted into tokens using a tokenizer such as Sentence-Piece (step 313). Thus every discrete unit of information becomes represented as a unique token. The system reserves a number of special tokens representing metainformation, for example, explicitly stating the type of information that will follow a token (e.g. imaging features, omics features) or denoting a time step or otherwise temporal information. The system is pre-trained to create equivalent vector representations of these meta-tokens through masked pre-training, whereby the system must successfully predict/generate the various meta-tokens after they have been masked.

The token sequence must be converted (or "embedded") into a sequence of continuous vectors of a fixed dimensionality (e.g. 4-long) in order to be processed by the core Transformer layer of the machine learning system (described in FIG. 4). The embedding process uses a Bayesian skip-gram model and may be adapted for the specific healthcare use case: a pre-trained embedding model may be tuned on healthcare domain data from the healthcare platform, which trains the embedding model to cluster tokens in a particular manner in vector space, e.g. grouping similar or related tokens together (e.g. dry cough and severe cough), using knowledge graphs of medical concepts and terms as corrective feedback. This learned embedding process advantageously confers relevant relational information to the downstream layers of the Transformer stack and speeds up the rate of training and improves system performance. Analogously, the embedded vectors are then passed through a positional encoding layer (step 317), which has been adapted for the specific healthcare use case to impart temporal information on each vector. The process similarly includes concatenating positional information in a learned manner, through earlier pre-training on time series or sequential healthcare data through masking temporal tokens. In this way, token sequences and later their continuous vector representations, enter the core encoder layers of the Transformer with relational and temporal information. Both of these steps are critical to the system accurately outputting predictions and recommendations like diagnoses, risk, treatment recommendations and so forth.

Once the tokens are embedded as continuous vectors with positional information, they enter the first encoder layer of the core Transformer and then pass through the neural network layers until a final softmax layer which outputs predicted probability distributions across multiple classes (described further below). In one embodiment, the system is trained through supervised learning using (1) clinical actions taken by humans or (2) clinical outcomes, as ground truth output targets (non-exhaustive examples). Illustratively, when using human clinical actions, the target output in each case is the full set of actions and inactions taken by the human clinician, represented as a probability vector spanning multiple classes, where each class represents a single action, inaction or prediction. The loss for each class is calculated by multiplying the predicted class probability by minus natural log of the ground truth probability of that class. The sum of these losses represent the cross-entropy, a loss function which the machine learning system attempts to minimize through successive training epochs. Additionally, class losses may be weighted to create a weighted cross-entropy, to take into account the relative importance of certain actions or predictions by the system (e.g. urgent referral for CT vs. issue a leaflet). Equation 1 below is the equation for non-weighted cross-entropy where p is the target probability distribution and q is the predicted probability distribution.

$$H(p, q) = -\sum_{x \in X} p(x) \log q(x) \qquad \text{Equation 1}$$

The neural network is then trained successively through epochs, with weights and biases of nodes updated with each epoch using the Adam backpropagation optimization, which attempts to minimize cross-entropy loss across successive epochs. In such a way, the neural network and machine learning system is trained, with human clinicians as the teachers.

FIG. 4 illustrates a transformer architecture. In this example, the machine learning system architecture comprises an ensemble of modified HydraNets that are optimized for multi-class classification of token sequences using Transformer neural networks, rather than for machine vision as per the original HydraNet architecture. Each HydraNet is itself an ensemble of neural networks. In this preferred example, the fusion layer 401 comprises multiple HydraNets specialized for extracting relevant features from specific input types 403 e.g. imaging, omic sequences, free text. For example, CNN and Semantic Segmentation is used for extracting relevant features from imaging such as XR, CT, MRI. In another example, a denoising autoencoder is used for extracting features from free text. The importance of this approach is that the networks in the fusion layer 401 all output to a shared feature ontology that is also understood by the downstream core representation HydraNet (which, in this example, is the Reformer/BERT-like neural network 405). This is achieved by pre-training the fusion layer 401 for multi-class prediction tasks for a predetermined reserved sequence of tokens, using consensus error versus structured data 407 and the ground truth output labels described previously as training targets. This approach therefore enables fusion of multimodal input sources and compression of very long input sequences containing mostly trivial information, into much smaller output sequences which are feature-rich and in a format compatible with the downstream Transformer neural networks. This dramatically improves system performance, inference compute cost, and reduces the size of the core representation layer 405, required for good performance. It allows for better parallelization of training by increasing modularity, allowing each input source to be trained and tested independently.

The embedding process of FIG. 3 is described in detail above. A token sequence from multimodal input sources is embedded 409 in the core representation layer 405 after receiving positional information through a learned positional encoding layer 410, and the outputs are passed to specialized neural networks 411 downstream that are pre-trained and optimized for specific task groups. For example: multivariate time series prediction requires representation of temporal features and needs to output predictions for future data points based on prior context. This benefits from a seq2seq Transformer architecture which includes both encoder and decoder stacks. For time series prediction, there may be multiple decoder stacks downstream which share inputs from upstream neural network(s). The task group may contain specialized temporal convolution layers designed to learn temporal representations and discover temporal structure across different time scales. Each downstream decoder stack may be pre-trained to predict different temporal features e.g. future risks of various types—symptoms, adherence, and so forth. This is a different task group to say, recommending the correct drug prescription or the right diagnosis. Through modularizing different task groups, and further specializing downstream neural networks 411 into lightweight task heads 413, each task group may be pre-trained and optimized for their specific downstream tasks independently, and achieve better performance versus a single neural network being used to generate all the final softmax outputs 415 of the machine learning system. Specialization downstream in the machine learning system also greatly increases compute efficiency and speed through enabling a specialized gating neural network to control which neural network branches are recruited, only recruiting those branches that are likely to be relevant for the final output.

A final integrator neural network receives task head outputs and blends these into a final output state, which is linearized into a number of softmax functions. Such softmax functions are modulated by a number of explicitly programmed rules, or expert systems, acting as safety "rails". Such rails are necessary and prudent in healthcare as a final safety and consistency check: for example, there are absolute contraindications for certain drugs; methotrexate and trimethoprim should not be prescribed together. The neural network and expert systems together comprise the blender/policy selection system 417, and generate the final modulated softmax outputs 415 of the machine learning system.

The architecture described also increases the explainability of the system to a level acceptable for healthcare applications through two mechanisms: (1) by increasing the number of human-parsible interfaces in the machine learning system—that is, the junctions between each neural network. Through backpropagation it is possible to discover how these intermediate outputs have influenced any given final system state; and (2) the core representation layer 405 (Reformer/BERT variant of the Transformer) also computes an alignment score matrix as a byproduct of scaled dot-product attention; this matrix represents the linearized correlations between input tokens and final output tokens. Such correlations may be displayed on the clinical dashboard to inform clinicians which input features the machine learning system considered key for making its given set of predictions and recommendations. This makes the decisions of the machine learning system explainable to human interpreters, critical for healthcare applications of ML. The new branch of the machine learning system is then subjected to a list of unit tests, to ensure that the system has now achieved good performance in the identified edge case failure class/domain. An illustrative example: if the edge case class is small cell lung cancer detection and management, unit tests would include—(1) F1 score performance when hemoptysis is not present (2) time to referral recommendation from first contact. Where unit tests fail, the sets are returned to the boosting step 122 at step 149 until the unit tests are passed or the training task is cancelled. Where the unit test is passed, a new test branch of the machine learning system is created at step 151.

In summary, in this preferred example, a highly specialized machine learning architecture and embedding schema is described, designed from the ground up for healthcare and the automation of diagnoses, management and follow-up. It addresses many of the shortcomings of existing approaches, including: (1) lack of explainability; (2) weak representation of temporal/sequential features; (3) prohibitively high compute costs; (4) high input noise; poor signal-to-noise ratio; and (5) lack of appropriate targets.

In order to test machine learning systems without putting patients at risk, shadow machine learning systems may be deployed. Shadow machine learning systems perform the same function as the live machine learning system, but do not output to patients. At step 153, a shadow machine learning system is deployed to run on the cloud service. The performance of the shadow machine learning system is evaluated on live and historical cases and its performance is compared to that of the live machine learning system and to human performance, to establish if it is appropriate to deploy the shadow system live. Where the evaluation is not passed (that is, a quality assurance team has not signed off on the evaluation), the shadow deployed branch of the machine learning system receives further training through further passes in the training engine: failures are identified, seeded, boosted and then trained for. When this occurs, a separate instance of the training engine loop analogous to that described above for the live machine learning system is applied at step 159. This continues until the QA team decides to stop the process or the shadow deployed branch passes QA evaluation.

At step 157, there is an automated clinical audit and live evaluation for evaluating collective human performance against the machine learning system performance, both in terms of process and outcome metrics. An example of a process metric as per the United Kingdom's National Health Service national guidelines: "offer all patients with a QRISK2 score of over 10%, the option of a statin". An example of an outcome metric: "adjusted patient reported outcome scores for asthma". This continuous evaluation process is an additional safety mechanism for ensuring the system is performing well.

If the shadow machine learning system branch passes QA evaluation, it may be deployed as a live machine learning system, ready for usage by user clients through inference (Step 105). This closes the flowchart loop.

The training and inference loop comprising inference, identifying failures, seeding edge cases, boosting edge case sets, and training the machine learning system is applied iteratively any number of times which continues to optimise and improve the performance of the healthcare system continuously, while serving user clients through inference.

Embodiments of the present disclosure may provide one or more of the following list of non-exhaustive, real world advantages. In beta testing of a limited set of early modules, 80% of captured cases could be managed remotely and asynchronously in less than one minute, leading to a 10 times workflow speed increase for clinicians and patients. With a regulator-approved fully autonomous healthcare AI, it is envisioned that 80% of clinician workload could be entirely passed on to the AI, which would handle the end-to-end process of diagnosis, testing, management, advice & coaching, and follow-up. Clinician time could be reserved for high-need patients who require intensive management. A large proportion of clinical trial work may be automated. Every clinical trial requires longitudinal follow-up of outcomes and potential side effects (currently a mostly manual process done by humans). The healthcare system may automatically follow up patients and predict potential side effects for early escalation. Curated data services may be provided for researchers. Researchers may also be allowed to lease time on the pre-trained machine learning system in order to answer any clinical research question. High throughput analytics may be provided for commissioners, insurers and governments in order to: increase cost efficiency of healthcare service provision and drug selection; evaluate the impact of various intervention programs in parallel; and use longitudinal outcomes to validate value-based care payments, enabling a shift away from an activity-driven health economy. Once integrated with multi-omics, the healthcare system may provide personalized healthcare services to individuals through, for example, a subscription or one-off payment, working in conjunction with doctors to deliver truly individualized treatment protocols based on the patient's disease subphenotype (each disease is in reality a normalized distribution of many slightly different syndromes/subphenotypes. For example, 30+ phenotypes of Type 2 Diabetes have already been identified).

According to another aspect of the present disclosure, there is provided a computer program for performing the method according to any of the embodiments described above.

According to another aspect, there is provided a healthcare system comprising: a machine learning system configured to: obtain, produce and label patient data relating to one or more patients; determine one or more predictions based on labelled patient data; receive, from a user, one or more user inputs labelling each of the one or more predictions as a success or a failure; generate training data based on the labelled patient data and one or more user inputs; and train the machine learning system based on the training data. The healthcare system may implement any embodiment of the method as described above. The optional features of the healthcare system set out below are analogous to those set out above in relation to the method for providing the healthcare system.

The healthcare system may comprise a healthcare platform such as that described above. The healthcare data platform may be configured to receive one or more patient inputs comprising patient data from the one or more patients in response to one or more patient questions and/or receive one or more telemetry inputs comprising patient data; and the machine learning system may be configured to obtain the patient data from the healthcare data platform.

The user may provide one or more additional patient questions to the one or more patients through the healthcare data platform in a plurality of instances, and the machine learning system may be configured to: cluster and classify the plurality of instances in which the user has provided one or more patient questions; and train the machine learning system to provide the one or more patient questions to the one or more patients.

The patient data obtained by the machine learning system may be pre-structured into a plurality of categories, the patient data in each category having explicit relationships.

The machine learning system may be further configured to output a patient output relating to the patient data based on a prediction of the one or more predictions to the one or more patients.

The machine learning system may be further configured to: determine a plurality of predictions based on the patient data; receive, from a user, a plurality of user inputs labelling each of the plurality of predictions as a success or a failure; and generate training data based on the labelled patient data and the plurality of user inputs. That is, the healthcare system is applicable to a plurality of users or patients, and indeed can obtain data and provide predictions relating to a plurality of users or patients.

The machine learning system may be further configured to: select one or more classes of user inputs of the plurality of user inputs labelling predictions as failures and dividing the selected user inputs into a training set and a test set; train a classifier based on the training set to predict if patient data should be classified as a further example of an edge case belonging to that class; and/or use the test set to validate the performance of the classifier.

The classifier may be configured to provide one or more questions to the user and/or the one or more patients in order to improve the quality and data density of training examples deemed relevant.

The machine learning system may be further configured to use an ensemble of neural networks to fuse multimodal inputs of patient data into a singular shared token ontology comprising one or more tokens and convert the one or more tokens to one to more continuous vector representations; and/or represent at least some of the multimodal patient data as latent space embeddings.

The machine learning system may be further configured to bucketize and tokenize at least some of the patient data into a standard medical token ontology.

The machine learning system may be further configured to receive a ground truth input from the user comprising one or more of: prescribing treatment; making a diagnosis; creating a care plan; arranging an appointment; or obtaining additional patient data. This is a non-exhaustive list of inputs. In this embodiment, a user input may be established as the ground truth.

In an alternative embodiment, a clinical outcome may be established as a ground truth output label for the training data.

The healthcare system may further comprise at least one shadow machine learning system configured to: determine one or more shadow predictions based on the patient data; receive, from the user, one or more user inputs labelling each of the one or more shadow predictions as a success or a failure; generate shadow training data based on the labelled patient data and the one or more user inputs; and train the at least one shadow machine learning system based on the shadow training data.

The machine learning system may be further configured to use one or more user inputs of the plurality of user inputs labelling predictions as successes to evaluate the performance of the machine learning system and determine whether or not regression of performance has taken place.

FIG. 5 illustrates an exemplary patient dashboard when a patient accesses the healthcare platform to input their data.

FIG. 6 illustrates an exemplary patient user interface when they complete a history using the healthcare platform. Patients input data concerning their medical problem into this interface, which is then sent to a clinician in the form of an abstracted clinical report for review and sign-off.

Figure 7:
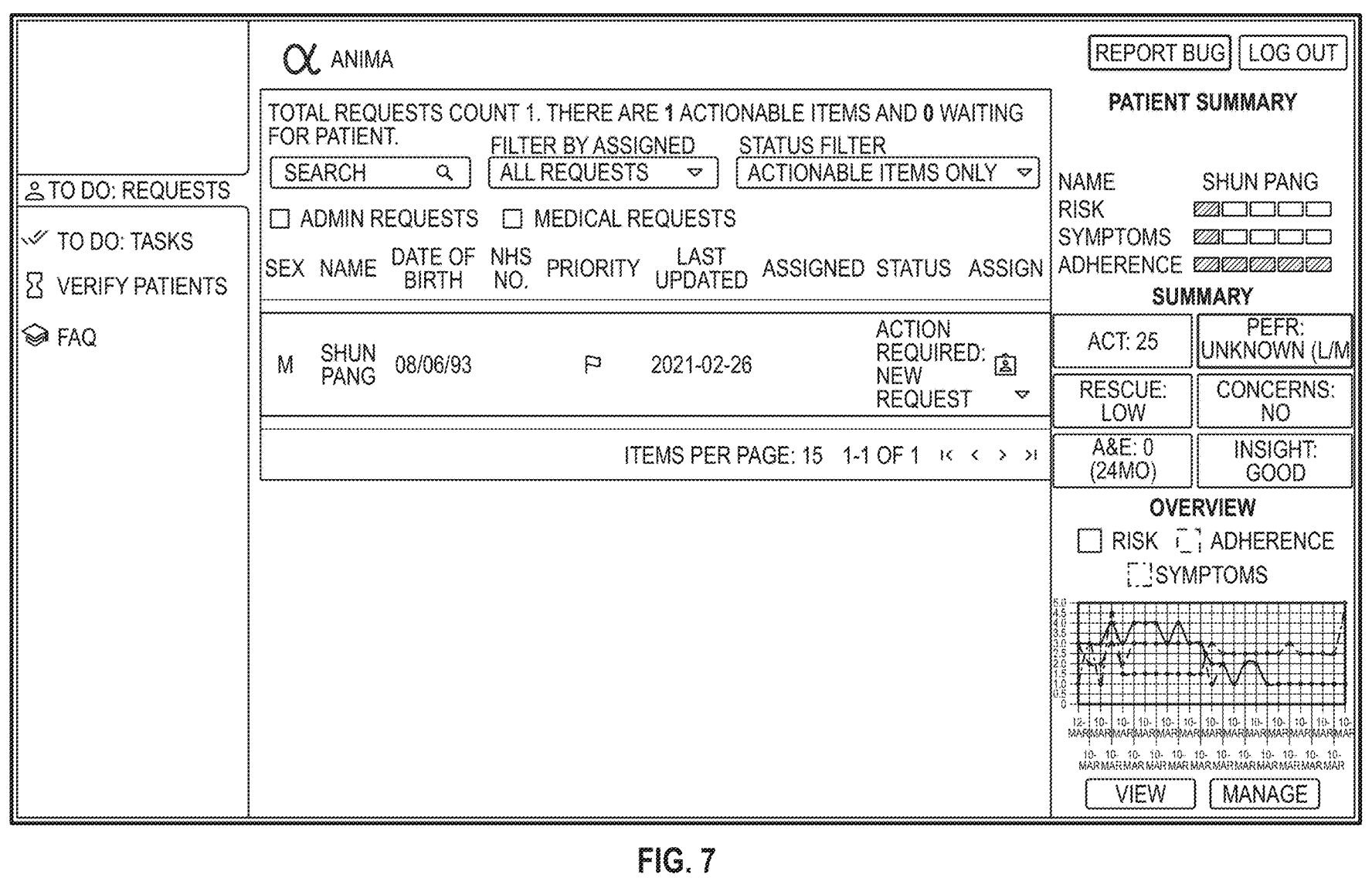

FIG. 7 illustrates an exemplary clinician dashboard when a clinician accesses the healthcare platform to receive and interact with output from the healthcare system, such as abstracted clinical reports. Under Patient Summary, different numbers of bars can indicate different values in terms of risk, symptoms, and adherence. For example, under "Risk," one of the five bars may be highlighted to indicate a risk value of 1. As another example, under "Symptoms," one of the five bars may be highlighted to indicate a symptom value of 1. As another example, under "Adherence," all five bars may be highlighted to indicate an Adherence value of 5.

FIG. 8 illustrates an exemplary secondary pop-up window that the clinician accesses to review the clinical report, predictions, recommendations and other processed patient

What is claimed is:

1. A computer-implemented method for training a prediction model of a healthcare system, the method comprising:
   obtaining patient data;
   inputting the patient data into the prediction model to determine a plurality of predictions;
   receiving, from a user, a plurality of user inputs labelling each of the plurality of predictions as a success or a failure;
   determining a plurality of classes based on the plurality of user inputs labelling predictions as failures, wherein determining the plurality of classes comprises:
      inputting the plurality of user inputs labelling the predictions as failures into an encoder model; and
      clustering, via the encoder model, the plurality of user inputs labelling the predictions as failures into the plurality of classes;
   generating new training data based on the selected class, wherein generating the new training data comprises:
      training a plurality of classifier models, each classifier model associated with a corresponding class of the plurality of classes;
      selecting a class of the plurality of classes, the class corresponding to a set of edge cases associated with a type of failure;
      receiving incoming patient data;
      inputting the incoming patient data into a classifier model corresponding to the selected class, the classifier model configured to predict if the incoming patient data is associated with the selected class; and
      in accordance with a prediction that the incoming patient data is associated with the selected class, associating the incoming patient data with the selected class; and
   training the prediction model of the healthcare system based on using the new training data.

2. The method according to claim 1, wherein:
   a healthcare data platform is configured to receive the patient data from one or more patients in response to one or more patient questions, one or more telemetry inputs, or a combination thereof; and
   the patient data is obtained via the healthcare data platform.

3. The method according to claim 2, further comprising:
   receiving, at a first time via the healthcare data platform from the user, a first set of patient questions presented to the one or more patients;
   receiving, at a second time via the healthcare platform from the user, a second set of patient questions presented to the one or patients;
   clustering the first set of patient questions and the second set of patient questions to produce one or more clusters of patient questions;
   classifying one or more clusters of patient questions; and
   training a machine learning model of the healthcare system to determine a third set of patient questions based on the classified one or more clusters of patient questions.

4. The method according to claim 1, wherein the patient data is pre-structured into a plurality of categories, the patient data in each category having explicit relationships.

5. The method according to claim 1, further comprising predicting, via the prediction model one or more patient outcomes; and
   determining a patient output based on the patient data and the one or more patient outcomes.

6. The method according to claim 1, further comprising:
   dividing the new training data into a new training set and a new test set;
   validating the performance of the classifier model based on the new test set,
   wherein training the prediction model is based on the new training set.

7. The method according to claim 1, further comprising:
   in response to classifying incoming patient data as associated with the class, providing one or more questions to a user associated with the incoming patient data;
   receiving, from the user, one or more answers to the one or more questions; and
   associating one or more new features with the class based on the one or more answers.

8. The method according to claim 1, further comprising preprocessing input data, the input data comprising the patient data and the incoming patient data, the preprocessing comprising:
   inputting the input data into an ensemble of neural networks, wherein the input data is associated with multimodal input sources;
   extracting, via the ensemble of neural networks, a plurality of patient features, wherein the plurality of patient features comprises a shared token ontology; and
   converting one or more tokens of the shared token ontology to one or more continuous vector representations.

9. The method according to claim 8, further comprising tokenizing a portion of the input data into a standard medical ontology.

10. The method according to claim 1, further comprising:
    performing Bayesian modelling of one or both of: an uncertainty distribution associated with an output of the prediction model; and a lateness of the prediction,
    wherein the new training data is further based on the Bayesian modeling.

11. The method according to claim 1, wherein receiving the plurality of user inputs labelling each of the plurality of predictions as a success or a failure comprises one or more of: prescribing treatment; making a diagnosis; creating a care plan; arranging an appointment; or obtaining additional patient data.

12. The method according to claim 1, wherein a clinical outcome is established as a ground truth output label for the new training data.

13. A method according to claim 1, further comprising:
    determining, via a shadow prediction model, one or more shadow predictions based on the new training data;
    receiving, from the user, one or more user inputs labelling each of the one or more shadow predictions as a success or a failure;
    generating shadow training data based on the labelled patient data and the one or more user inputs; and
    training the shadow prediction model based on the shadow training data.

14. The method according to claim 13, further comprising:
    evaluating a performance of the shadow prediction model using a second portion of user inputs labeling predictions as successes; and
    determining whether the shadow prediction model performs better than the prediction model;

in accordance with a determination that the shadow prediction model performs better than the prediction model, replacing the prediction model with the shadow prediction model; and in accordance with a determination that the shadow prediction model performs worse than the prediction model, continuing to train the shadow prediction model.

15. The method according to claim 1, further comprising boosting the class to include an overrepresentation of the type of failure compared to a general population.

16. A healthcare system comprising:

one or more electronic devices, the one or more electronic devices comprising a memory and one or more programs, wherein the one or more programs are stored in the memory and configured to be executed by the one or more electronic devices, the one or more programs including instructions for:

obtaining patient data;

inputting the patient data into the prediction model to determine a plurality of predictions;

receiving, from a user, a plurality of user inputs labelling each of the plurality of predictions as a success or a failure;

determining a plurality of classes based on the plurality of user inputs labelling predictions as failures, wherein determining the plurality of classes comprises:

inputting the plurality of user inputs labelling the predictions as failures into an encoder model; and clustering, via the encoder model, the plurality of user inputs labelling the predictions as failures into the plurality of classes;

generating new training data based on the selected class, wherein generating the new training data comprises:

training a plurality of classifier models, each classifier model associated with a corresponding class of the plurality of classes;

selecting a class of the plurality of classes, the class corresponding to a set of edge cases associated with a type of failure;

receiving incoming patient data;

inputting the incoming patient data into a classifier model corresponding to the selected class, the classifier model configured to predict if the incoming patient data is associated with the selected class; and in accordance with a prediction that the incoming patient data is associated with the selected class, associating the incoming patient data with the selected class; and training the prediction model of the healthcare system using the new training data.

* * * * *